United States Patent
Rong et al.

(10) Patent No.: US 11,988,772 B2
(45) Date of Patent: May 21, 2024

(54) REMOTE RECOVERY OF ACOUSTIC SIGNALS FROM PASSIVE SOURCES

(71) Applicant: ARIZONA BOARD OF REGENTS ON BEHALF OF ARIZONA STATE UNIVERSITY, Scottsdale, AZ (US)

(72) Inventors: Yu Rong, Tempe, AZ (US); Daniel W. Bliss, Phoenix, AZ (US); Sharanya Srinivas, Cambridge, MA (US); Adarsh Venkataramani, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 17/773,503

(22) PCT Filed: Oct. 30, 2020

(86) PCT No.: PCT/US2020/058326
§ 371 (c)(1),
(2) Date: Apr. 29, 2022

(87) PCT Pub. No.: WO2021/087337
PCT Pub. Date: May 6, 2021

(65) Prior Publication Data
US 2023/0003835 A1    Jan. 5, 2023

Related U.S. Application Data

(60) Provisional application No. 62/929,140, filed on Nov. 1, 2019.

(51) Int. Cl.
*G01S 7/41*     (2006.01)
*A61B 5/05*     (2021.01)
(Continued)

(52) U.S. Cl.
CPC ............... *G01S 7/415* (2013.01); *G01H 9/00* (2013.01); *G01S 7/295* (2013.01); *G01S 13/0209* (2013.01); *A61B 5/05* (2013.01)

(58) Field of Classification Search
CPC ...... G01S 7/415; G01S 7/295; G01S 13/0209; G01S 7/412; G01S 7/2883; G01S 7/292;
(Continued)

(56) References Cited

U.S. PATENT DOCUMENTS 3,110,897 A  *  11/1963  Laurent ................... G01S 13/24
                                                              342/131
3,719,945 A  *  3/1973   Sletten .................... G01S 7/414
                                                              342/201

(Continued)

FOREIGN PATENT DOCUMENTS

CN    106264501 A         1/2017
EP         3739356 A1 *  11/2020  .............. G01P 15/18
(Continued)

OTHER PUBLICATIONS

Non-Final Office Action for U.S. Appl. No. 17/277,596, dated Aug. 18, 2023, 10 pages.
(Continued)

*Primary Examiner* — Nuzhat Pervin
(74) *Attorney, Agent, or Firm* — Withrow & Terranova, P.L.L.C.; Vincent K. Gustafson

(57) ABSTRACT

Remote recovery of acoustic signals from passive sources is provided. Wideband radars, such as ultra-wideband (UWB) radars can detect minute surface displacements for vibrometry applications. Embodiments described herein remotely sense sound and recover acoustic signals from vibrating sources using radars. Early research in this domain only demonstrated single sound source recovery using narrowband millimeter wave radars in direct line-of-sight sce-
(Continued)

narios. Instead, by using wideband radars (e.g., X band UWB radars), multiple sources separated in ranges are observed and their signals isolated and recovered. Additionally, the see-through ability of microwave signals is leveraged to extend this technology to surveillance of targets obstructed by barriers. Blind surveillance is achieved by reconstructing audio from a passive object which is merely in proximity of the sound source using clever radar and audio processing techniques.

9 Claims, 13 Drawing Sheets

(51) Int. Cl.
  *G01H 9/00* (2006.01)
  *G01S 7/295* (2006.01)
  *G01S 13/02* (2006.01)

(58) Field of Classification Search
  CPC ......... G01S 13/42; G01S 7/414; G01S 13/56; G01S 13/88; G01H 9/00; A61B 5/05
  USPC ........................................................ 342/192
  See application file for complete search history.

(56) References Cited

U.S. PATENT DOCUMENTS

| | | | | |
|---|---|---|---|---|
| 4,803,489 A * | 2/1989 | Giori | ...................... | G01S 7/414 342/192 |
| 4,860,014 A * | 8/1989 | Shores | .................. | G01S 13/325 342/195 |
| 5,424,749 A * | 6/1995 | Richmond | .............. | F41H 13/00 342/194 |
| 5,565,872 A * | 10/1996 | Prevatt | ..................... | G01S 13/50 342/192 |
| 5,828,331 A * | 10/1998 | Harper | .................... | G01S 7/352 342/22 |
| 6,026,340 A * | 2/2000 | Corrado | ............ | B60R 21/01536 701/47 |
| 6,861,974 B1 * | 3/2005 | Poe | ....................... | G01S 7/4008 342/134 |
| 7,567,200 B1 * | 7/2009 | Osterweil | ............... | G01S 13/56 342/28 |
| 7,782,256 B2 * | 8/2010 | Smith | .................... | G01S 13/726 342/453 |
| 7,916,066 B1 * | 3/2011 | Osterweil | ............. | A61B 5/1117 382/115 |
| 8,068,051 B1 * | 11/2011 | Osterweil | ................ | G01S 7/006 340/573.5 |
| 8,681,585 B2 * | 3/2014 | Dahl | ..................... | G01S 7/5273 367/99 |
| 8,686,362 B2 * | 4/2014 | Bakhtiari | ............. | A61B 5/0507 250/338.1 |
| 8,687,689 B2 * | 4/2014 | Baraniuk | ............... | H03M 13/11 375/240.01 |
| 8,712,069 B1 * | 4/2014 | Murgia | .................. | H04R 3/005 702/92 |
| 9,164,167 B2 | 10/2015 | Hyde et al. | | |
| 9,297,886 B1 * | 3/2016 | Mountcastle | ........... | G01S 13/52 |
| 9,329,728 B2 * | 5/2016 | Dahl | ........................ | G06F 3/043 |
| 9,341,706 B2 * | 5/2016 | Ward | ....................... | G01S 7/412 |
| 9,357,293 B2 * | 5/2016 | Claussen | ................. | H04R 3/005 |
| 9,568,595 B2 * | 2/2017 | Zack | ..................... | A61B 5/7282 |
| 9,775,520 B2 * | 10/2017 | Tran | ......................... | A61B 5/01 |
| 10,019,998 B2 * | 7/2018 | Bilobrov | ............... | G10L 19/018 |
| 10,063,965 B2 * | 8/2018 | Kim | .......................... | G01S 5/18 |
| 10,078,328 B1 * | 9/2018 | Slater | ................. | H01L 31/0547 |
| 10,197,667 B2 * | 2/2019 | Reil | ...................... | G01S 7/4052 |
| 10,209,825 B2 * | 2/2019 | Sheng | .................... | G06F 3/0436 |
| 10,228,449 B2 * | 3/2019 | Nguyen | ............ | H04L 25/03305 |
| 10,234,543 B2 * | 3/2019 | Mazzaro | ................. | G01S 7/354 |
| 10,234,552 B1 * | 3/2019 | Jazayeri | ................ | G01S 13/885 |
| 10,310,073 B1 | 6/2019 | Santra et al. | | |
| 10,436,888 B2 * | 10/2019 | Li | .......................... | G01S 13/886 |
| 10,481,245 B2 * | 11/2019 | LaPat | ....................... | G01S 13/18 |
| 10,955,524 B2 * | 3/2021 | Crane | ................. | G01S 13/5246 |
| 11,240,579 B2 * | 2/2022 | Jumbe | .................... | A61B 5/412 |
| 11,624,821 B2 * | 4/2023 | Rappaport | .............. | G01S 13/42 342/179 |
| 2005/0024257 A1 * | 2/2005 | Britton | ..................... | G01S 7/412 342/22 |
| 2005/0168336 A1 * | 8/2005 | Donskoy | ............... | A01M 1/026 340/539.11 |
| 2006/0253278 A1 * | 11/2006 | Furst-Yust | .............. | H04S 1/002 704/209 |
| 2008/0077015 A1 * | 3/2008 | Boric-Lubecke | ..... | G01S 13/888 600/453 |
| 2008/0088508 A1 * | 4/2008 | Smith | .................... | G01S 13/878 342/453 |
| 2008/0135762 A1 | 6/2008 | Villanucci et al. | | |
| 2008/0151694 A1 | 6/2008 | Slater | | |
| 2009/0135086 A1 * | 5/2009 | Fuller | ................... | G01S 13/885 343/909 |
| 2009/0203972 A1 | 8/2009 | Heneghan et al. | | |
| 2009/0222226 A1 * | 9/2009 | Baraniuk | ............... | H03M 13/11 702/66 |
| 2010/0011845 A1 * | 1/2010 | Laugharn, Jr. | .......... | B01F 31/87 73/64.53 |
| 2010/0152600 A1 * | 6/2010 | Droitcour | .............. | A61B 5/1113 600/534 |
| 2010/0290063 A1 * | 11/2010 | Bakhtiari | .............. | A61B 5/1126 356/614 |
| 2011/0102247 A1 * | 5/2011 | Pauli | ...................... | G01S 13/937 342/159 |
| 2013/0053653 A1 | 2/2013 | Cuddihy et al. | | |
| 2013/0300473 A1 * | 11/2013 | Bass | ...................... | H03L 7/0805 327/158 |
| 2013/0300573 A1 | 11/2013 | Brown et al. | | |
| 2014/0194793 A1 * | 7/2014 | Nakata | ..................... | G01S 13/87 601/48 |
| 2014/0212986 A1 | 7/2014 | Angelescu et al. | | |
| 2014/0312986 A1 * | 10/2014 | Edelstein | ................ | H01P 3/006 333/33 |
| 2014/0378809 A1 * | 12/2014 | Weitnauer | ................ | A61B 5/24 600/407 |
| 2015/0319540 A1 | 11/2015 | Rubinstein et al. | | |
| 2016/0022204 A1 | 1/2016 | Mostov | | |
| 2016/0054438 A1 * | 2/2016 | Patole | ........................ | G01S 7/35 342/127 |
| 2016/0089052 A1 | 3/2016 | Cho et al. | | |
| 2016/0274218 A1 * | 9/2016 | McCaughey | ........... | G01S 7/414 |
| 2016/0341814 A1 * | 11/2016 | Nguyen | ............ | H04L 25/03305 |
| 2017/0131335 A1 * | 5/2017 | Pratt | .................... | H04B 17/391 |
| 2017/0173262 A1 * | 6/2017 | Veltz | ..................... | G16H 20/17 |
| 2018/0000408 A1 | 1/2018 | Heinrich et al. | | |
| 2019/0059746 A1 | 2/2019 | McMahon et al. | | |
| 2019/0064364 A1 * | 2/2019 | Boysel | .................... | G05D 1/027 |
| 2020/0025876 A1 * | 1/2020 | Chuang | ................. | G01S 13/88 |
| 2020/0025911 A1 * | 1/2020 | Rappaport | ............... | H01Q 3/26 |
| 2020/0196866 A1 | 6/2020 | Chiou et al. | | |
| 2021/0018610 A1 * | 1/2021 | Babakhani | .............. | G01S 13/581 |
| 2021/0093203 A1 | 4/2021 | Zhong et al. | | |
| 2021/0096208 A1 * | 4/2021 | Rittenschober | ......... | G01S 3/801 |
| 2021/0353156 A1 | 11/2021 | Rong et al. | | |
| 2022/0142478 A1 | 5/2022 | Bliss et al. | | |
| 2022/0373646 A1 | 11/2022 | Nguyen et al. | | |
| 2023/0000396 A1 | 1/2023 | Coffey et al. | | |

FOREIGN PATENT DOCUMENTS

| | | | | |
|---|---|---|---|---|
| EP | 3479140 B1 * | 4/2022 | ......... | G01S 13/0209 |
| EP | 4162865 A1 * | 4/2023 | ........... | A61B 5/0205 |
| JP | 2022153626 A * | 10/2022 | ............... | G06F 3/01 |
| WO | 0116554 A2 | 3/2001 | | |
| WO | 0116554 A3 | 9/2001 | | |
| WO | 2005091014 A1 | 9/2005 | | |
| WO | 2008001092 A2 | 1/2008 | | |
| WO | 2012055148 A1 | 5/2012 | | |

(56) References Cited

FOREIGN PATENT DOCUMENTS

| WO | 2017180985 A1 | 10/2017 | | |
|---|---|---|---|---|
| WO | 2018050913 A1 | 3/2018 | | |
| WO | WO-2018050913 A1 * | 3/2018 | ........... | A61B 5/0816 |
| WO | 2018213757 A1 | 11/2018 | | |
| WO | 2018234394 A1 | 12/2018 | | |
| WO | 2021086809 A1 | 5/2021 | | |

OTHER PUBLICATIONS

Notice of Allowance for U.S. Appl. No. 17/772,844, dated Feb. 23, 2023, 9 pages.
Anderson, N. et al., "A 118-mW Pulse-Based Radar SoC in 55-nm CMOS for Non-Contact Human Vital Signs Detection," IEEE Journal of Solid-State Circuits, vol. 52, No. 12, Dec. 2017, IEEE, pp. 3421-3432.
Aumann, H.M. et al., "Doppler radar microphone with logarithmic square-law detector," Electronics Letters, vol. 52, No. 12, Jun. 2016, pp. 1061-1063.
Avargel, Y. et al., "Speech measurements using a laser Doppler vibrometer sensor: Application to speech enhancement," 2011 Joint Workshop on Hands-free Speech Communication and Microphone Arrays, May 30-Jun. 1, 2011, Edinburgh, UK, IEEE.
Chazal, P. et al., "Sleep/wake measurement using a noncontact biomotion sensor," Journal of Sleep Research, vol. 20, No. 2, Aug. 2010, pp. 356-366.
Chernov, N. et al., "Least Squares Fitting of Circles," Journal of Mathematical Imaging and Vision, vol. 23, No. 3, Nov. 2005, pp. 239-252.
Chung, K-Y. et al., "Noncontact Sleep Study by Multi-Modal Sensor Fusion," Sensors, vol. 17, No. 7, Jul. 2017, MDPI, 17 pages.
Davis, A. et al., "The Visual Microphone: Passive Recovery of Sound from Video," ACM Transactions on Graphics, vol. 33, No. 4, Jul. 2014, 10 pages.
Guan, S. et al., "Automated DC Offset Calibration Strategy for Structural Health Monitoring Based on Portable CW Radar Sensor," IEEE Transactions on Instrumentation and Measurement, vol. 63, No. 12, Dec. 2014, IEEE, pp. 3111-3118.
Geisheimer, J.L. et al., "A Surface Vibration Electromagnetic Speech Sensor," Multi-modal Speech Recognition Workshop 2002, Jun. 2002, Georgia Tech Research Institute, Atlanta Sensors and Electromagnetic Applications Lab, 5 pages.
Immoreev, I. et al., "UWB Radar for Patient Monitoring," IEEE Aerospace and Electronic Systems Magazine, vol. 23, Issue 11, Nov. 2008, IEEE, 8 pages.
Jiao, M. et al., "A Novel Radar Sensor for the Non-Contact Detection of Speech Signals," Sensors, vol. 10, No. 5, May 2010, pp. 4622-4633.
Lazaro, A. et al., "Analysis of Vital Signs Monitoring Using an IR-UWB Radar," Progress In Electromagnetics Research, vol. 100, Jan. 2010, pp. 265-284.
Lee, J.-M. et al., "Comparison of Wearable Trackers' Ability to Estimate Sleep," International Journal of Environmental Research and Public Health, vol. 15, No. 6, Jun. 2018, MDPI, 13 pages.
Li, C. et al., "Complex Signal Demodulation and Random Body Movement Cancellation Techniques for Non-contact Vital Sign Detection," 2008 IEEE MTT-S International Microwave Symposium Digest, Jun. 15-20, 2008, Atlanta, GA, USA, IEEE, 4 pages.
Mercuri, M. et al., "Vital-sign monitoring and spatial tracking of multiple people using a contactless radar-based sensor," Nature Electronics, vol. 2, Jun. 2019, pp. 252-262.
Nam, Y. et al., "Sleep Monitoring Based on a Tri-Axial Accelerometer and a Pressure Sensor," Sensors, vol. 16, No. 5, May 2016, MDPI, 14 pages.
Park, B.-K. et al., "Arctangent Demodulation With DC Offset Compensation in Quadrature Doppler Radar Receiver Systems," IEEE Transactions on Microwave Theory and Techniques, vol. 55, No. 5, May 2007, IEEE, pp. 1073-1079.
Rahmati, M. et al., "SSFB: Signal-Space-Frequency Beamforming for Underwater Acoustic Video Transmission," 2017 IEEE 14th International Conference on Mobile Ad Hoc and Sensor Systems (MASS), Oct. 22-25, 2017, Orlando, FL, USA, IEEE, pp. 180-188.
Ren, L. et al., "Noncontact Heartbeat Detection using UWB Impulse Doppler Radar," 2015 IEEE Topical Conference on Biomedical Wireless Technologies, Networks, and Sensing Systems (BioWireleSS), Jan. 25-28, 2015, San Diego, CA, IEEE, 3 pages.
Ren, L. et al., "Phase-Based Methods for Heart Rate Detection Using UWB Impulse Doppler Radar," IEEE Transactions on Microwave Theory and Techniques, vol. 64, Issue 10, Oct. 2016, IEEE, 13 pages.
Rong, Y. et al., "Harmonics-Based Multiple Heartbeat Detection at Equal Distance using UWB Impulse Radar," 2018 IEEE Radar Conference (RadarConf18), Apr. 23-27, 2018, Oklahoma City, OK, USA, IEEE, 5 pages.
Rong, Y. et al., "Remote Sensing for Vital Information Based on Spectral-Domain Harmonic Signatures," IEEE Transactions on Aerospace and Electronic Systems, vol. 55, No. 6, May 2019, IEEE, 12 pages.
Rong, Y. "Remote Sensing For Vital Signs Monitoring Using Advanced Radar Signal Processing Techniques," A Dissertation Presented in Partial Fulfillment of the Requirements for the Degree Doctor of Philosophy, Arizona State University, Dec. 2018, 117 pages.
Rong, Y. et al., "Smart Homes: See Multiple Heartbeats Through Wall Using Wireless Signals," 2019 Radar Conference (RadarConf), Apr. 2019, Boston, MA, USA, IEEE, 6 pages.
Rothberg, S. et al., "Laser vibrometry: Pseudo-vibrations," Journal of Sound and Vibration, Dec. 1989, Elsevier, 18 pages.
Savage, H.O. et al., "Development and validation of a novel non-contact monitor of nocturnal respiration for dentifying sleep-disordered breathing in patients with heart failure," ESC Heart Failure, vol. 3, No. 3, Sep. 2016, John Wiley & Sons, pp. 212-219.
Staderini, E.M., "UWB Radars in Medicine," IEEE Aerospace and Electronic Systems Magazine, vol. 17, No. 1, Feb. 2002, pp. 13-18.
Tian, Y. et al., "Smart radar sensor for speech detection and enhancement," Sensors and Actuators A: Physical, vol. 191, Mar. 2013, Elsevier, pp. 99-104.
Viswanathan, V. et al., "Noise-immune multisensor speech input: formal subjective testing in operational conditions," International Conference on Acoustics, Speech, and Signal Processing, May 23-26, 1989, Glasgow, UK, IEEE, pp. 373-376.
Viswanathan, V. et al., "Noise-immune speech transduction using multiple sensors," IEEE International Conference on Acoustics, Speech, and Signal Processing (ICASSP'85), Apr. 26-29, 1985, Tampa, FL, USA, IEEE, 4 pages.
Yacchirema, D.C., "A Smart System for Sleep Monitoring by Integrating IoT With Big Data Analytics," IEEE Access, vol. 6, Jun. 2018, 16 pages.
Zhao, H. et al., "A Portable 24-GHz Auditory Radar for Non-contact Speech Sensing with Background Noise Rejection and Directional Discrimination," 2016 IEEE MTT-S International Microwave Symposium (IMS), May 22-27, 2016, San Francisco, CA, USA, IEEE, 4 pages.
Invitation to Pay Additional Fees for International Patent Application No. PCT/US2019/053425, dated Nov. 27, 2019, 2 pages.
International Search Report and Written Opinion for International Patent Application No. PCT/US2019/053425, dated Jan. 30, 2020, 10 pages.
International Preliminary Report on Patentability for International Patent Application No. PCT/US2019/053425, dated Apr. 15, 2021, 7 pages.
International Search Report and Written Opinion for International Patent Application No. PCT/US2020/057452, dated Feb. 12, 2021, 11 pages.
International Search Report and Written Opinion for International Patent Application No. PCT/US2020/058326, dated Feb. 3, 2021, 13 pages.
Author Unknown, "XeThru X4," available as early as Apr. 40, 2019, accessed Jun. 9, 2022 from https://www.radartutorial.eu/19.kartei/13.labs/karte009.en.html, 1 page.
Lee, J. et al., "Sleep Monitoring System Using Kinect Sensor," International Journal of Distributed Sensor Networks, vol. 11, No. 10, Oct. 2015, Hindawi Publishing Corporation, 10 pages.

(56) References Cited

OTHER PUBLICATIONS

Ma, Y. et al., "Speech Recovery Based On Auditory Radar and Webcam," 2019 IEEE MTT-S International Microwave Biomedical Conference (IMBioC), May 6-8, 2019, Nanjing, China, IEEE, 3 pages.
Extended European Search Report for European Patent Application No. 20882810.3, dated Nov. 22, 2022, 9 pages.
Final Office Action for U.S. Appl. No. 17/277,596, mailed Dec. 28, 2023, 10 pages.

* cited by examiner

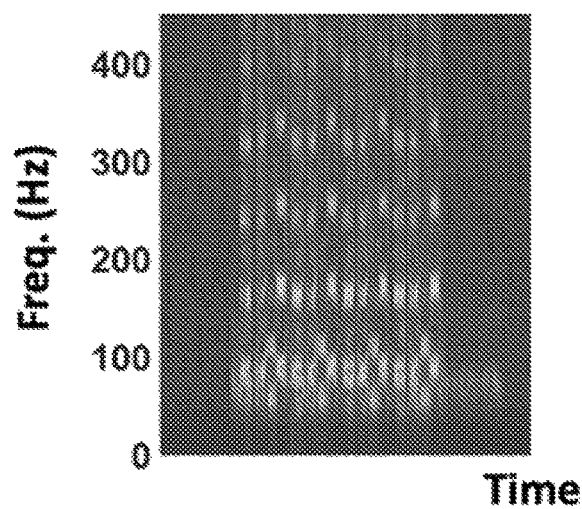
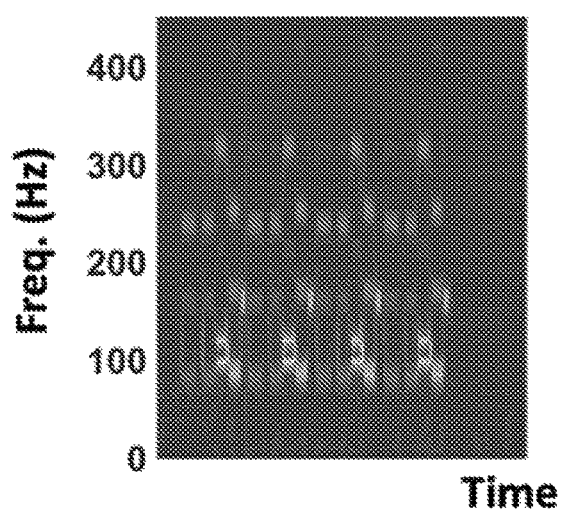
FIG. 6A     FIG. 6B
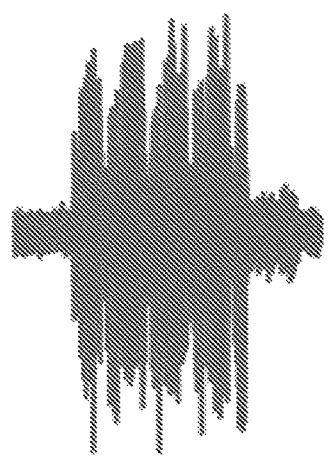
FIG. 6C     FIG. 6D

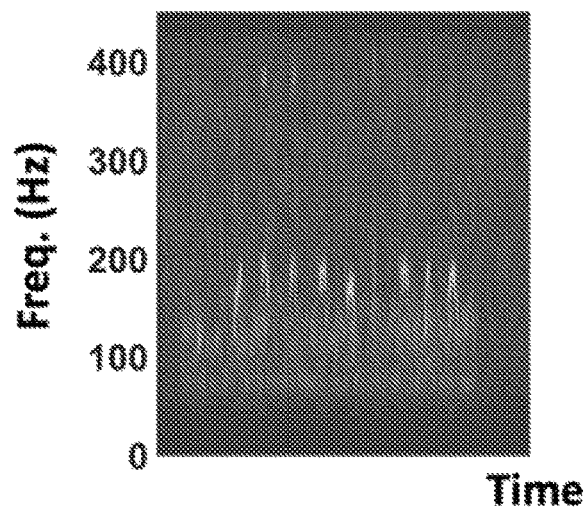 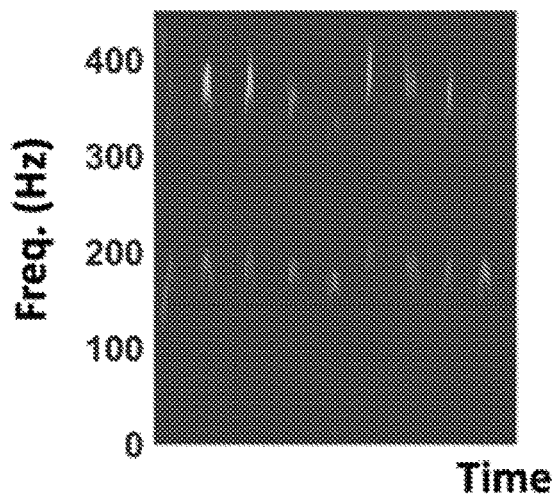
FIG. 10A  FIG. 10B
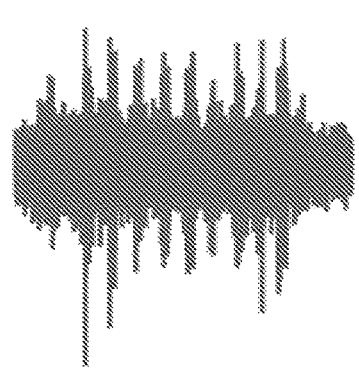 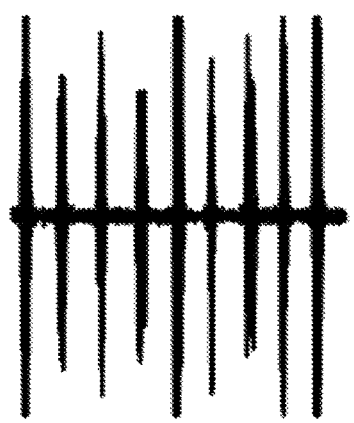
FIG. 10C  FIG. 10D

REMOTE RECOVERY OF ACOUSTIC SIGNALS FROM PASSIVE SOURCES

RELATED APPLICATIONS

This application is a 35 USC 371 national phase filing of International Application No. PCT/US2020/058326, filed Oct. 30, 2020, which claims the benefit of U.S. Provisional Patent Application No. 62/929,140, filed Nov. 1, 2019, the disclosures of which are incorporated herein by reference in their entireties.

FIELD OF THE DISCLOSURE

The present disclosure relates to acoustic signal detection through radio frequency (RF) signals.

BACKGROUND

Radars have always been an integral part of industrial automation, surveillance security and health monitoring systems. Previously, their ability to detect minute surface displacements has been exploited for vibrometry applications such as speech recovery. Similarly, surface skin motions have been extracted for vital signs detection and even through-wall cardiac sensing.

Recovery of acoustic signals from surface vibrations using distinct sensors has been a topic of interest for a few decades now. When sound propagates through a medium, it creates pressure waves that induce surface displacements. Feasibility of using radars to remotely sense sound has been illustrated for speech retrieval. Radar sensing has also been illustrated for generic acoustic signals using different millimeter wave radars and several improvements have been proposed to radar receivers. A variety of speech recovery methods have also been proposed to handle noisy backgrounds.

These previous approaches employed narrowband millimeter wave Doppler radars for sound sensing and have been limited to single acoustic source recovery in direct line-of-sight scenarios.

SUMMARY

Remote recovery of acoustic signals from passive sources is provided. Wideband radars, such as ultra-wideband (UWB) radars can detect minute surface displacements for vibrometry applications. Embodiments described herein remotely sense sound and recover acoustic signals from vibrating sources using radars. Early research in this domain only demonstrated single sound source recovery using narrowband millimeter wave radars in direct line-of-sight scenarios. Instead, by using wideband radars (e.g., X band UWB radars), multiple sources separated in ranges are observed and their signals isolated and recovered. Additionally, the see-through ability of microwave signals is leveraged to extend this technology to surveillance of targets obstructed by barriers. Blind surveillance is achieved by reconstructing audio from a passive object which is merely in proximity of the sound source using clever radar and audio processing techniques.

Embodiments disclosed herein use a radio frequency (RF) radar sensor, such as a wideband radar sensor (e.g., X band UWB pulse Doppler radar sensor), to measure surface displacement of a vibrating surface. A radar response signal is received, from which a motion signal is extracted. An acoustic signal is reconstructed from the motion signal using signal processing techniques, such as a fast Fourier transform (FFT)-based time-frequency signal processing technique. In some examples, the vibrating surface can be a passively vibrating source (e.g., one excited indirectly, such as by a non-line-of-sight active acoustic source). Some examples can isolate acoustic signals from multiple active sources. Some examples can also exploit a see-through ability of the radar signal to recover acoustic signals.

An exemplary embodiment provides a method for remote recovery of an acoustic signal. The method includes transmitting a radar signal toward a vibrating surface and receiving an RF response signal corresponding to the radar signal. The method further includes extracting a motion signal from the RF response signal, determining spatial information corresponding to the vibrating surface from the motion signal, and reconstructing an acoustic signal from the motion signal using the spatial information.

Another exemplary embodiment provides an RF device. The RF device includes a radar sensor and a processing circuit coupled to the radar sensor. The radar sensor is configured to receive an RF response signal to a radar signal. The processing circuit is configured to recover an acoustic signal by extracting a motion signal for one or more vibrating surfaces from the RF response signal, determining spatial information corresponding to the one or more vibrating surfaces from the motion signal, and using the spatial information to recover the acoustic signal from the motion signal.

Another exemplary embodiment provides a system for remote recovery of an acoustic signal. The system includes a radar sensor, a database, and a processing circuit coupled to the database. The radar sensor is configured to receive an RF response signal to a radar signal. The database is configured to store the RF response signal. The processing circuit is configured to extract a motion signal for a vibrating surface from the RF response signal, determine spatial information corresponding to the vibrating surface from the motion signal, the spatial information comprising at least one of a range to the vibrating surface, an angle to the vibrating surface, and a Doppler frequency shift associated with the vibrating surface, and reconstruct the acoustic signal from the motion signal using the spatial information.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

FIG. 6A is a spectrogram of a radar result for remote recovery of the acoustic signal of FIG. 5.

FIG. 6B is a spectrogram of the original audio signal.

FIG. 6C is a graphical representation of the radar recovered audio waveform from the radar result of FIG. 5.

FIG. 6D is a graphical representation of the original audio waveform.

FIG. 10A is a spectrogram of a radar result for remote recovery of the acoustic signal from FIG. 9.

FIG. 10B is a spectrogram of the original audio signal.

FIG. 10C is a graphical representation of the radar recovered audio waveform.

FIG. 10D is a graphical representation of the original audio waveform.

DETAILED DESCRIPTION

Figure 1A:
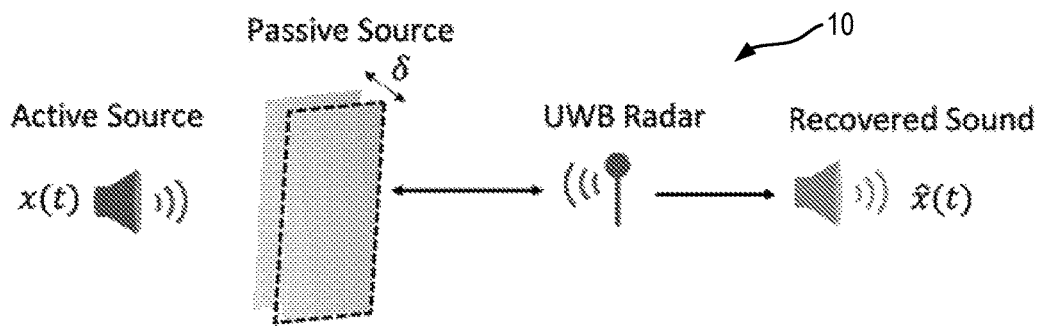
FIG. 1A is a schematic diagram of an exemplary system for remote recovery of an acoustic signal, illustrating observation of surface displacement of a passive object in the proximity of an active source.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Remote recovery of acoustic signals from passive sources is provided. Wideband radars, such as ultra-wideband (UWB) radars can detect minute surface displacements for vibrometry applications. Embodiments described herein remotely sense sound and recover acoustic signals from vibrating sources using radars. Early research in this domain only demonstrated single sound source recovery using narrowband millimeter wave radars in direct line-of-sight scenarios. Instead, by using wideband radars (e.g., X band UWB radars), multiple sources separated in ranges are observed and their signals isolated and recovered. Additionally, the see-through ability of microwave signals is leveraged to extend this technology to surveillance of targets obstructed by barriers. Blind surveillance is achieved by reconstructing audio from a passive object which is merely in proximity of the sound source using clever radar and audio processing techniques.

Embodiments disclosed herein use a radio frequency (RF) radar sensor, such as a wideband radar sensor (e.g., X band UWB pulse Doppler radar sensor), to measure surface displacement of a vibrating surface. A radar response signal is received, from which a motion signal is extracted. An acoustic signal is reconstructed from the motion signal using signal processing techniques, such as a fast Fourier transform (FFT)-based time-frequency signal processing technique. In some examples, the vibrating surface can be a passively vibrating source (e.g., one excited indirectly, such as by a non-line-of-sight active acoustic source). Some examples can isolate acoustic signals from multiple active sources. Some examples can also exploit a see-through ability of the radar signal to recover acoustic signals.

I. Introduction

Previous approaches employed narrowband millimeter wave Doppler radars to single acoustic source recovery in direct line-of-sight scenarios. Embodiments of the present disclosure instead use wideband radar sensors (e.g., a UWB radar operating at X frequency band) as an RF microphone but in much more complex environments.

Figure 1B:
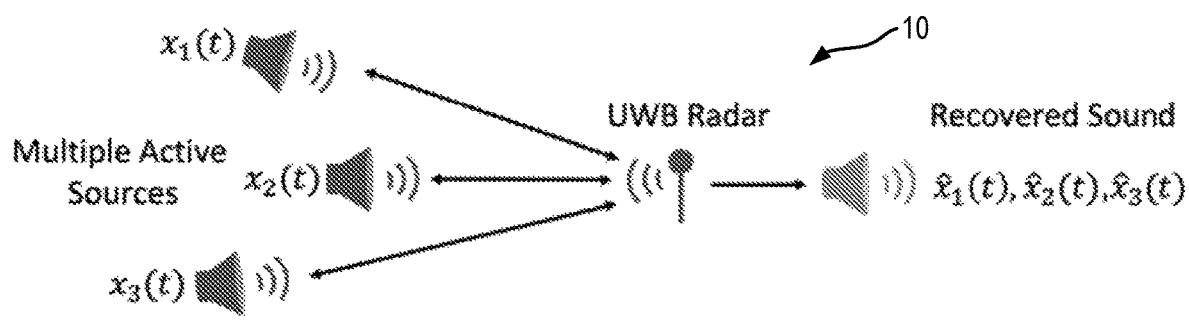
FIG. 1B is a schematic diagram of the system of FIG. 1A, illustrating detection and isolation of acoustic signals by observing surface displacement of multiple sound sources separated in different ranges to the radar.
Figure 1C:
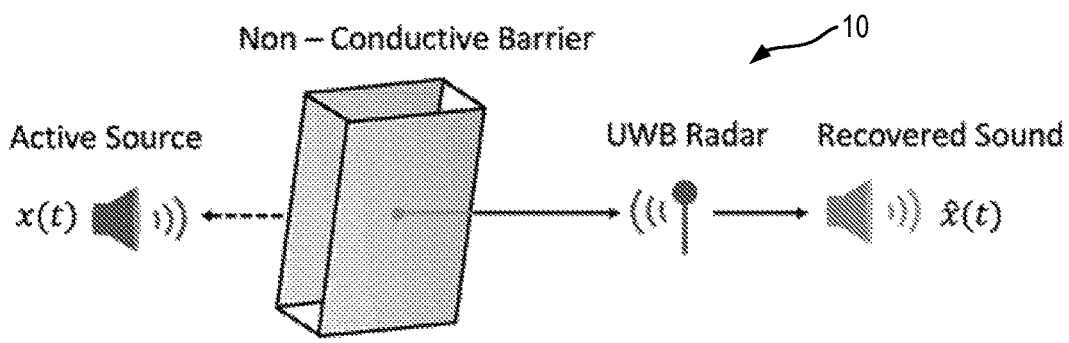
FIG. 1C is a schematic diagram of the system of FIG. 1A, illustrating recovery of an acoustic signal from a sound source obstructed by a dielectric medium.

FIGS. 1A-1C illustrate three unique evaluation setups used to demonstrate the success of the technology described herein. FIG. 1A is a schematic diagram of an exemplary system 10 for remote recovery of an acoustic signal, illustrating observation of surface displacement of a passive object in the proximity of an active source. FIG. 1B is a schematic diagram of the system of FIG. 1A, illustrating detection and isolation of acoustic signals by observing surface displacement of multiple sound sources separated in different ranges to the radar. FIG. 1C is a schematic diagram of the system of FIG. 1A, illustrating recovery of an acoustic signal from a sound source obstructed by a dielectric medium. This disclosure analyzes the spectrum and waveform of a reference source and recovered signals to illustrate workings of proposed processing techniques.

II. Radar Processing

Figure 2:
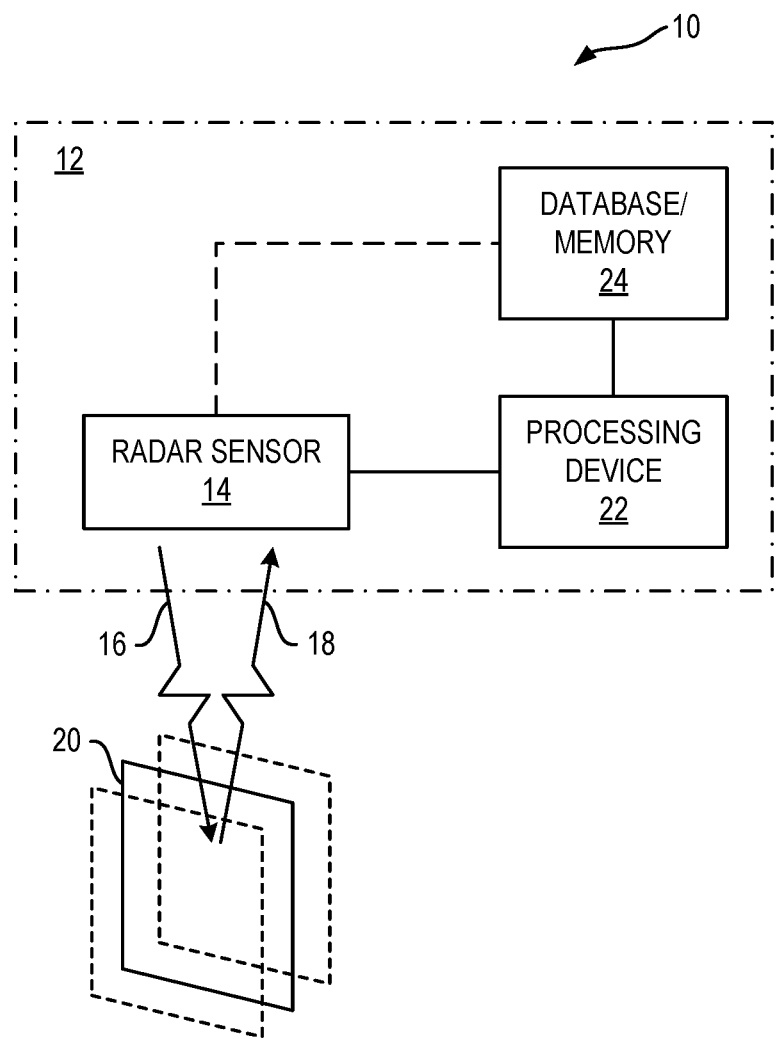
FIG. 2 is a schematic diagram of the system of FIGS. 1A-1C, which includes a radio frequency (RF) device for acoustic recovery using wideband radar.

FIG. 2 is a schematic diagram of the system 10 of FIGS. 1A-1C, which includes an RF device 12 for acoustic recovery using wideband radar. In an exemplary aspect, the RF device 12 includes a radar sensor 14 which transmits a radar signal 16 and receives an RF response signal 18 to the radar signal 16 after interaction with (e.g., reflection/refraction from) one or more vibrating surfaces 20. The vibrating surfaces 20 represent any surface which may vibrate with an acoustic signal, such as an active acoustic source or a passive acoustic source, such as in the examples illustrated in FIGS. 1A-1C. The RF device 12 further includes a processing device 22 for processing and analyzing the RF response signal 18 to recover one or more acoustic signals. Generally, the RF device 12 further includes a database or memory 24 for storing instructions and/or data, which is coupled to the processing device 22 (and optionally coupled to the radar sensor 14). The RF device 12 may include additional components, such as discussed in Section VI below.

In an exemplary aspect, the radar sensor is a wideband radar, and the radar signal 16 is a wideband radar signal, such as an X band UWB impulse signal. It should be understood that other signals may be used (e.g., a non-impulse radar signal) in an appropriate electromagnetic frequency (e.g., terrestrial radio, microwave, mmWave, optical, etc.). In some examples, the radar sensor 14 receives the RF response signal 18 without sending the radar signal 16 (e.g., the radar signal 16 is sent from another component of the RF device 12 or from another transmitter device).

In the illustrated embodiment, the system 10 for remote recovery of an acoustic signal primarily includes the RF device 12. In other embodiments, the system 10 includes the components of the RF device 12 as two or more separate devices. For example, the processing device 22 and/or the database/memory 24 may be incorporated in a remote server, with minimal or no signal processing being performed at the radar sensor 14.

This section elaborates on proposed processing steps that make detection and recovery of audio signals using radars (e.g., the radar sensor 14) possible. First, models for radar return for an environment are established. Next, how radar processing alters the model analytically is described. Given that Doppler shift is extracted in slow time from the pre-processing stage, exemplary audio recovery methods are elaborated.

A. Signal Model

An impulse radar emits same narrow pulse at every pulse repetition interval. When reflected off a vibrating target (e.g., the vibrating surface 20), the received pulse is modulated in phase and magnitude. Inspecting and extracting meaningful information from such backscattered signal is termed radar 'sensing'. The RF response of surface vibrations of the object is modeled as a superposition of responses from discrete, dynamic scattering centers. The i-th scattering center is parameterized by reflectivity coefficient $\rho_i(t)$ and radial distance $d_i(t)$ from the radar sensor, which vary as a function of time t. The received composite signal is modeled as:

$$y(\tau, t) = \sum_i^N \rho_i(t) p(\tau - \tau_{d_i}(t)) \quad \text{Equation 1}$$

$$= \sum_i^N \rho_i(t) p\left(\tau - 2\frac{d_i(t)}{c}\right) \quad \text{Equation 2}$$

where N is the number of scattering centers and $p(\tau)$ is the transmitted pulse, c denotes the speed of light. Note that t and $\tau$ are two different time scales. The former is often referred as slow-time sampling interval and is related to the pulse repetition interval. The latter time scale is referred as fast-time sampling interval and is often associated with ADC sampling interval providing distance information.

The direct RF sampled signal is then down converted to the complex baseband and is represented as:

$$y_b(t) = y(t,\tau) e^{-j2\pi F_c \tau} \quad \text{Equation 3}$$

where $F_c$ denotes the nominal operating frequency.

B. Radar Processing

Figure 3:
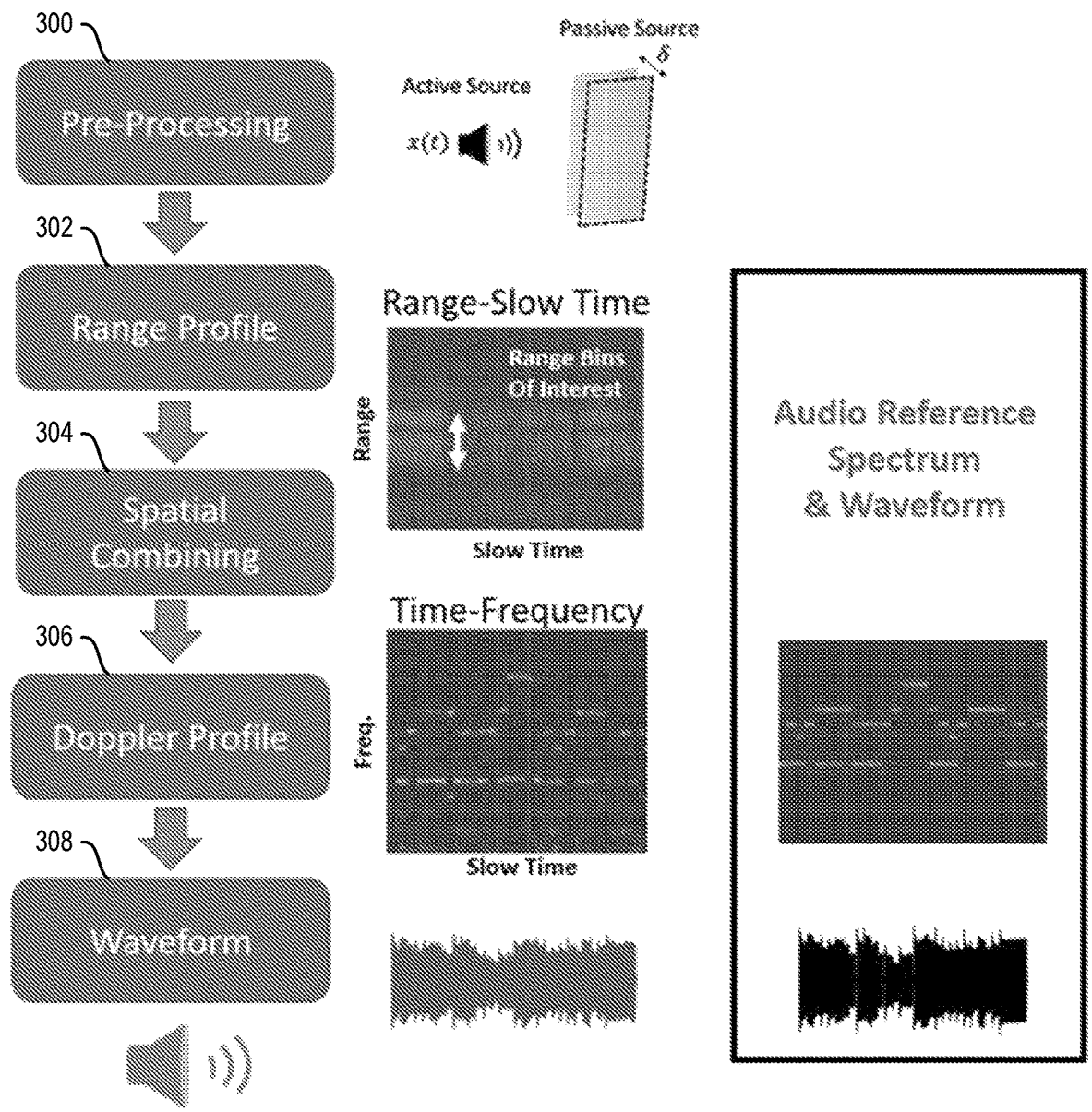
FIG. 3 is a graphical flowchart of an exemplary process for audio signal extraction from a backscattered radar return.

FIG. 3 is a graphical flowchart of an exemplary process for audio signal extraction from a backscattered radar return (e.g., the RF response signal 18). At a pre-processing stage (block 300), motion filtering is implemented to remove a static background. In an exemplary aspect, the received radar return is organized in two-dimensional (2-D) matrix format with one direction corresponding to the slow-time samples t and the other direction to the fast-time/range samples T. By stacking range samples column-wise (block 302), vibration profiles are revealed in a range-slow time heatmap. The most significant energy indicates where the surface motion occurs.

In order to capture all the local motions, multiple range bins of interest are spatially combined into a single time series $\dot{y}_b(t)$ (block 304) and a composite vibration profile (e.g., a Doppler profile) is obtained (block 306). Then, time-varying spectral features are inspected through time frequency analysis. For visualization purposes of this study, a few edited audio sound clips that have very distinct spectral and temporal features are selected as shown in the results section. The radar recovered acoustic wave is constructed (block 308) by the proposed audio recovery method in Section III. The goal is to extract good quality audio samples from radar signals and then these audible samples are played out by an audio device so that human can hear and recognize it.

III. Audio Signal Processing

Sound is produced when molecules inside a medium are exerted by an internal or external force (certain embodiments consider only external forces). More elaborately, kinetic energy generated due to motion of an external object is transferred into surrounding molecules in vicinity of the object. This energy travels through the medium as a longitudinal wave and is heard as sound. In the context of radar processing, rate of object displacement is the Doppler frequency/velocity of object. The Doppler frequency is computed by taking a Fourier transform across slow time. In radar vibrometry, a short-time Fourier transform (STFT) is instead computed across slow time for a selected number of range bins.

Figure 4:
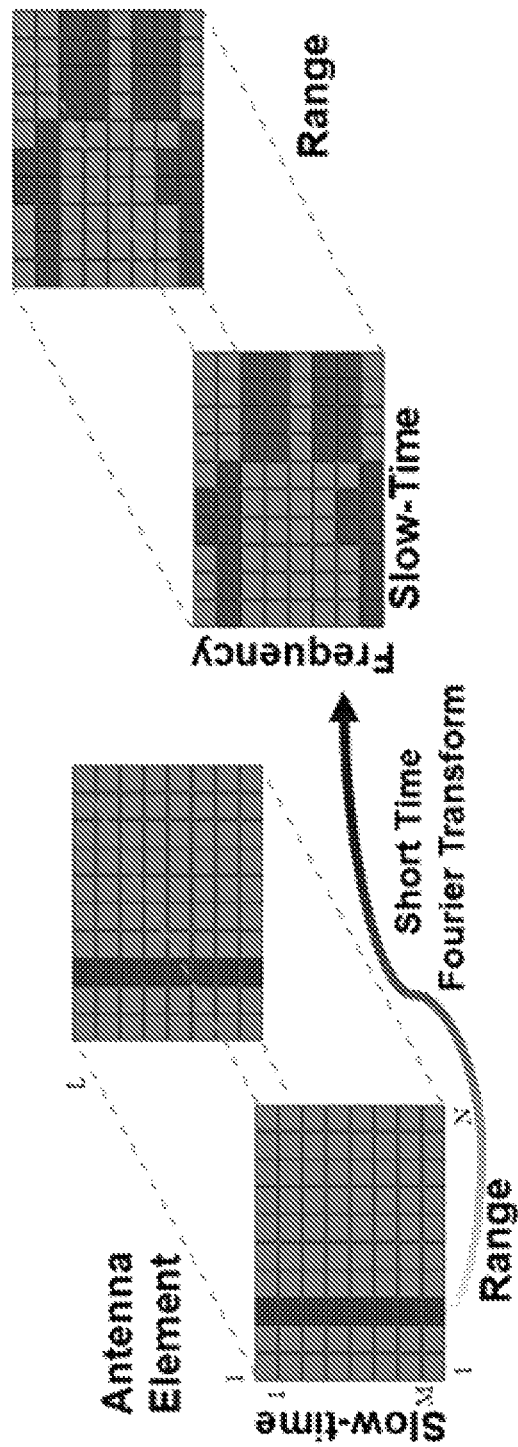
FIG. 4 is a schematic diagram of a radar data matrix which includes micro-displacements corresponding to an acoustic signal.

FIG. 4 is a graphical representation of an analogy of a radar data matrix (which includes micro-displacements corresponding to an acoustic signal) with sound production. Using this analogy, radar vibrometry can be interpreted as hearing Doppler frequency of the object in time.

During radar processing for a given slow time period, the received complex baseband waveform for a closely spaced set of range bins contains all vibration information from detected sources. STFT is then operated on the spatially combined complex baseband waveform $\dot{y}_b(t)$:

$$S_y(t,f;h) = \text{STFT}(\dot{y}_b(t)) = \int \dot{y}_b(\kappa) h^*(\kappa-t) e^{-j2\pi f\kappa} d\kappa \quad \text{Equation 4}$$

Equivalently, it may be represented in the frequency spectrum as:

$$S_y(t,f;h) = S_{(y,f)}(t,f;h) + S_{(y,-f)}(t,-f;h) \quad \text{Equation 5}$$

where $S_y(t, f; h)$ is the STFT of the signal $\dot{y}_b$ using a window function h(t). It is to be noted that the bandwidth of $S_y(t, f; h)$ is always band limited by maximum measurable Doppler frequency. The band limited signal inherently reduces ambient noise to give high quality sound. However, the STFT of complex baseband signal $\dot{y}_b(t)$ is generally not symmetric, $S_{(y,f)} \neq S_{(y,-f)}$. This poses a significant challenge in recovery. This symmetry issue is addressed by emphasizing that vibrations are physical phenomena and are transmitted/acquired as real signals. To this end, a conjugate symmetry is enforced such that $S_{(y,f)}(t, f; h) = S_{(y,-f)}^*(t, -f; h)$, and the resulting inverse STFT transformed waveform is deemed to be a real-valued signal x(t).

The chosen mirroring spectrum is based on power density comparison, higher power gives better audible sound. Thus, if $S_{(y,f)}(t,f;h)$ contains more energy than $S_{(y,-f)}(t,-f;h)$ in the spectral range of interest, such as:

$$\Sigma_t \Sigma_{f_1}{}^{f_2} |S_{(y,f)}(t,f;h)|^2 > \Sigma_t \Sigma_{f_1}{}^{f_2} |S_{(y,-f)}(t,-f;h)|^2 \quad \text{Equation 6}$$

then $S_{(y,f)}(t, f; h)$ is a better candidate for mirroring and vice versa. Hence Equation 5 reduces to:

$$x(t) = \text{STFT}^{-1}\{S_{(y,f)}(t,f;h) + S_{(y,-f)}^*(t,-f;h)\} \quad \text{Equation 7}$$

where g(t) is a window function used in inverse STFT. Additional processing steps by using filters on $S_y(t, f; h)$ may be performed to reduce noise, however for clarity those details are omitted. Under the unity energy assumption on window functions h(t) and g(t), Equation 7 simplifies into:

$$x(t) = 2\text{Re}\{\dot{y}_b(t)\} \quad \text{Equation 8}$$

specifically when both STFT and inverse STFT (ISTFT) windows are identical the resulting sound waveform generated is the real part of $\dot{y}_b(t)$, $x(t) = 2\text{Re}\{\dot{y}_b(t)\}$. If $S_{(y,-f)}(t, -f; h)$ is used in for mirroring in Equation 7, the resulting sound waveform is the imaginary part of $\dot{y}_b(t)$, $x(t) = 2\text{Imag}\{\dot{y}_b(t)\}$. The resulting range averaged complex baseband waveform contains most of the vibration information for production of sound. Evaluations on passive and active sources as well as discussion of these results are in the next section.

IV. Evaluation Results

Successful radar vibrometry is demonstrated for a multitude of tests using a UWB radar with 2 gigahertz (GHz) bandwidth operating around 10 GHz with slow-time frame rate 1000 hertz (Hz). Three distinct evaluation setups are constructed—1) recover source audio by observing a passive source, 2) detect and isolate signal from two sources separated in space and 3) retrieve audio from a source obstructed by a non-conductive barrier such as a wall (see FIGS. 1A-1C).

A. Evaluation Setup 1: Passive Source

Figure 5:
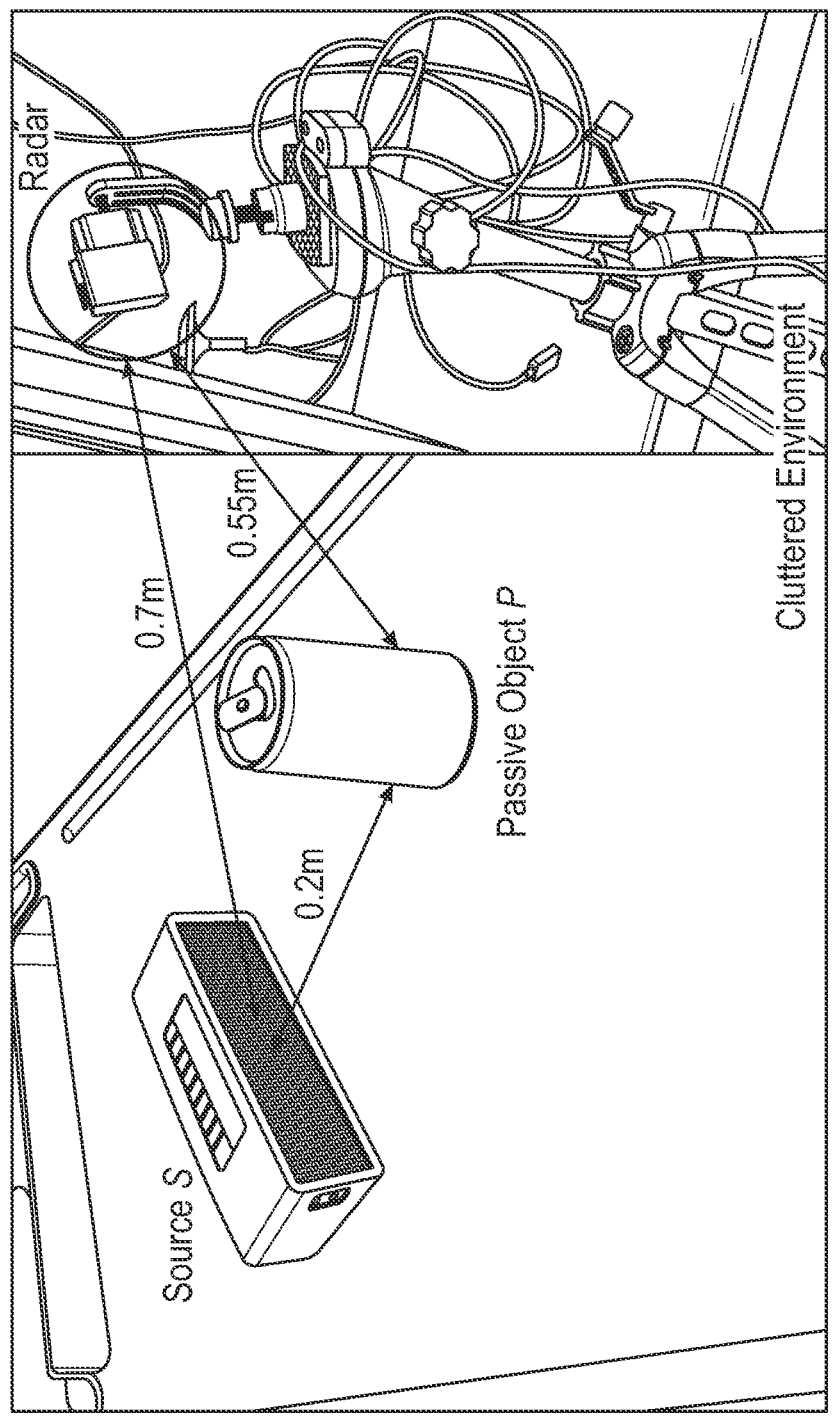
FIG. 5 is an image of a first evaluation setup, which recovers an acoustic signal by observing surface displacement of a passive source.

FIG. 5 is an image of the first evaluation setup, which recovers an acoustic signal by observing surface displacement of a passive source. A passive object is exposed to an audio source in a cluttered environment, and surface vibrations of the object as a result of its proximity to the source are studied via UWB radar. Here, the audio source is a speaker labeled S and the object under observation is an empty aluminum soda can P, both of which are separated by a small distance of about 15 cm.

FIG. 6A is a spectrogram of a radar result for remote recovery of the acoustic signal of FIG. 5. FIG. 6B is a spectrogram of the original audio signal. The micro-displacements dominated by the passive object are collected from the range bins of interest and processed. An improved radar spectrogram is obtained since all the major spectral features (bright dots at higher frequencies and square shapes at lower frequencies) seen in FIG. 6B are recovered in FIG. 6A. Additionally, higher order harmonic frequency components and intermodulations are observed.

FIG. 6C is a graphical representation of the radar recovered audio waveform from the radar result of FIG. 5. FIG. 6D is a graphical representation of the original audio waveform. The radar recovered waveform is also consistent with the majority of the temporal structure of the original audio waveform.

B. Evaluation Setup 2: Multiple Sources

Figure 7:
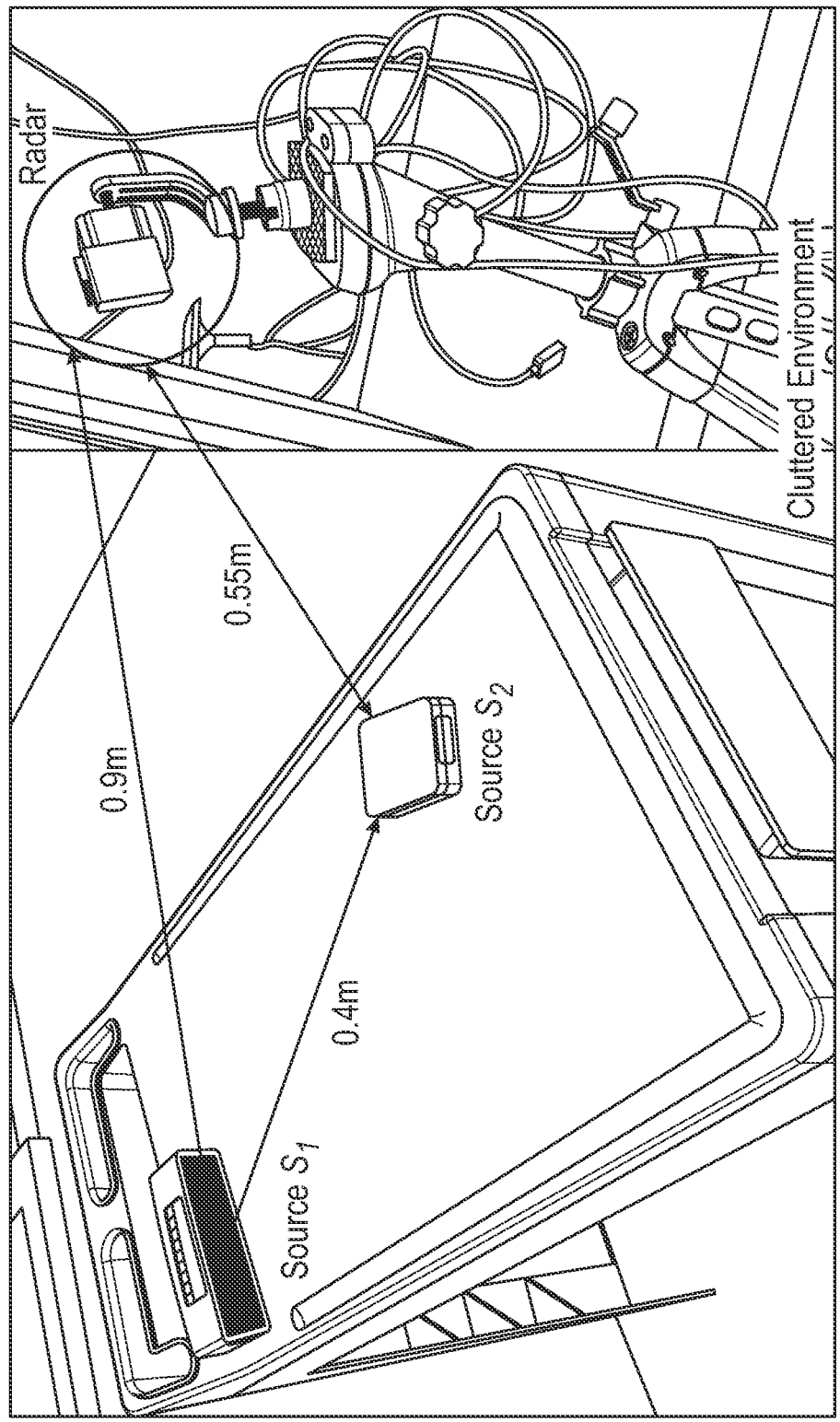
FIG. 7 is an image of a second evaluation setup, which recovers multiple acoustic signals by observing and isolating surface displacement of two active sources at different ranges.

FIG. 7 is an image of the second evaluation setup, which recovers multiple acoustic signals by observing and isolating surface displacement of two active sources at different ranges. This setup demonstrates the ability to isolate audio signals for different vibrating sources from the radar return signal in non-ideal environments by clever radar processing. An evaluation setup was constructed where two audio sources $S_1$ and $S_2$, separated in space, are being illuminated by a UWB radar. To add interest, two sound sources (two commercially available speakers) are used, playing two pre-edited sound files. The two sources are loudly playing different audio signals $x_1(t)$ and $x_2(t)$ respectively, which are recovered using methods outlined earlier.

Figures 8A, 8B:
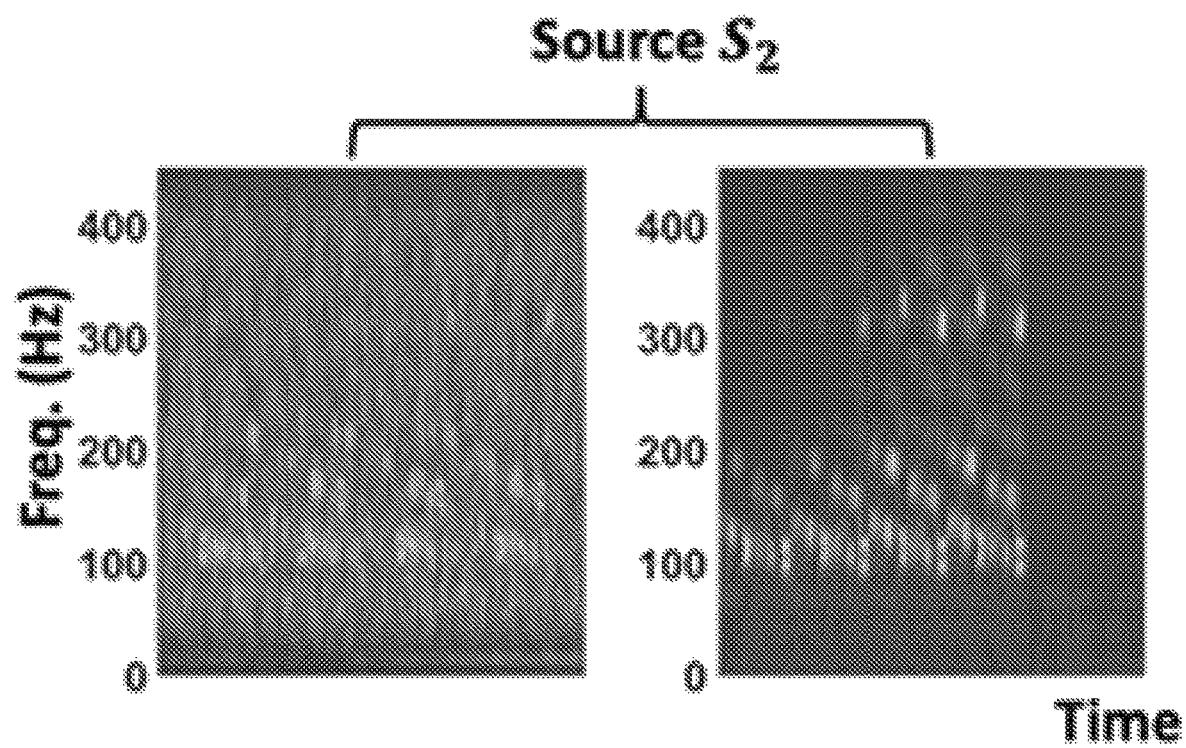
FIG. 8A is a spectrogram of a radar result for remote recovery of the acoustic signal from the closer sound source $S_2$ of FIG. 7.
FIG. 8B is a spectrogram of the original audio signal from sound source $S_2$.
Figures 8C, 8D:
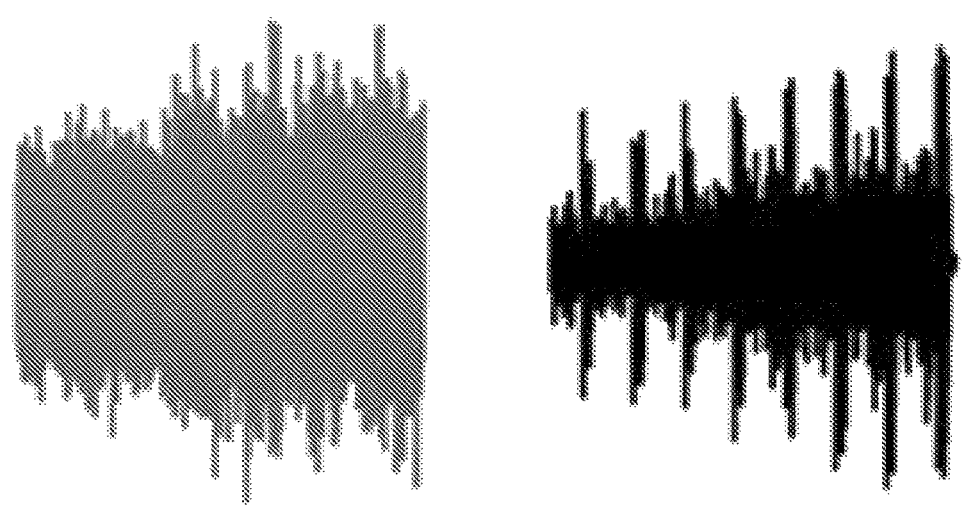
FIG. 8C is a graphical representation of the radar recovered audio waveform $\hat{x}_2(t)$ from sound source $S_2$.
FIG. 8D is a graphical representation of the original audio waveform $x_2(t)$ from sound source $S_2$.

FIG. 8A is a spectrogram of a radar result for remote recovery of the acoustic signal from the closer sound source $S_2$ of FIG. 7. FIG. 8B is a spectrogram of the original audio signal from sound source $S_2$. FIG. 8C is a graphical representation of the radar recovered audio waveform $\hat{x}_2(t)$ from sound source $S_2$. FIG. 8D is a graphical representation of the original audio waveform $x_2(t)$ from sound source $S_2$.

Figures 8E, 8F:
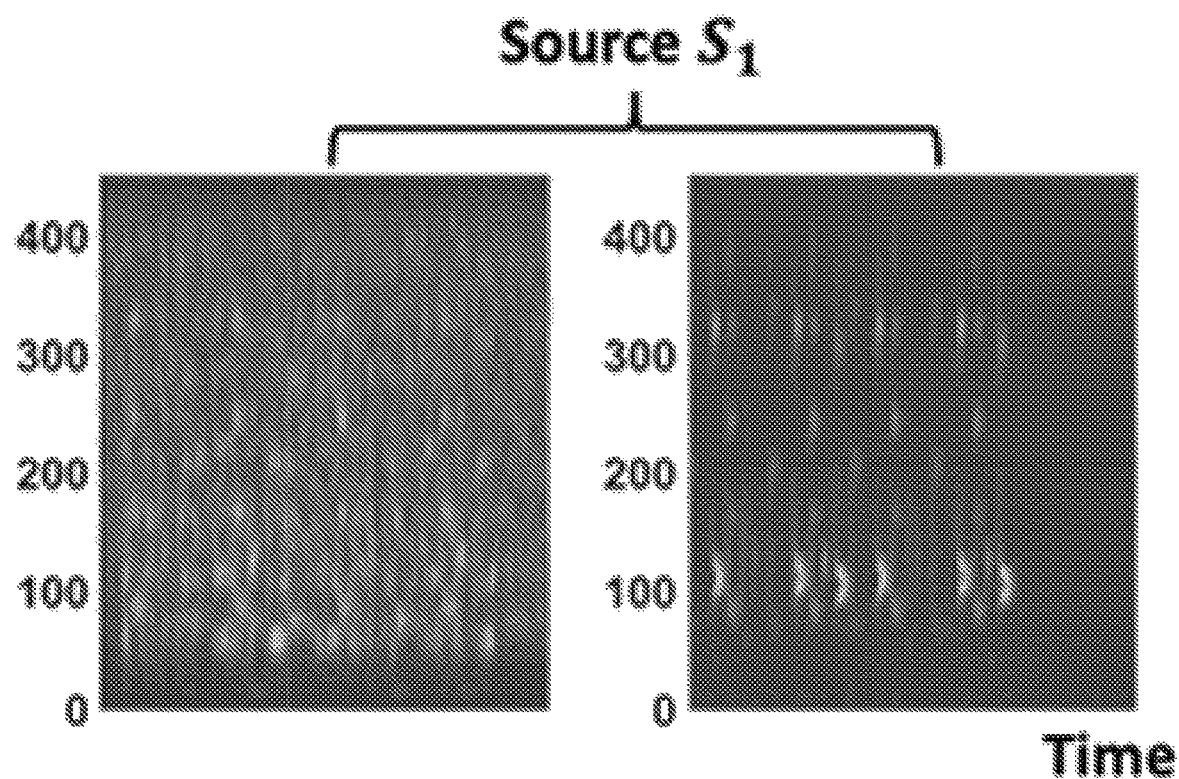
FIG. 8E is a spectrogram of a radar result for remote recovery of the acoustic signal from the further sound source $S_1$ of FIG. 7.
FIG. 8F is a spectrogram of the original audio signal from sound source $S_1$.
Figures 8G, 8H:
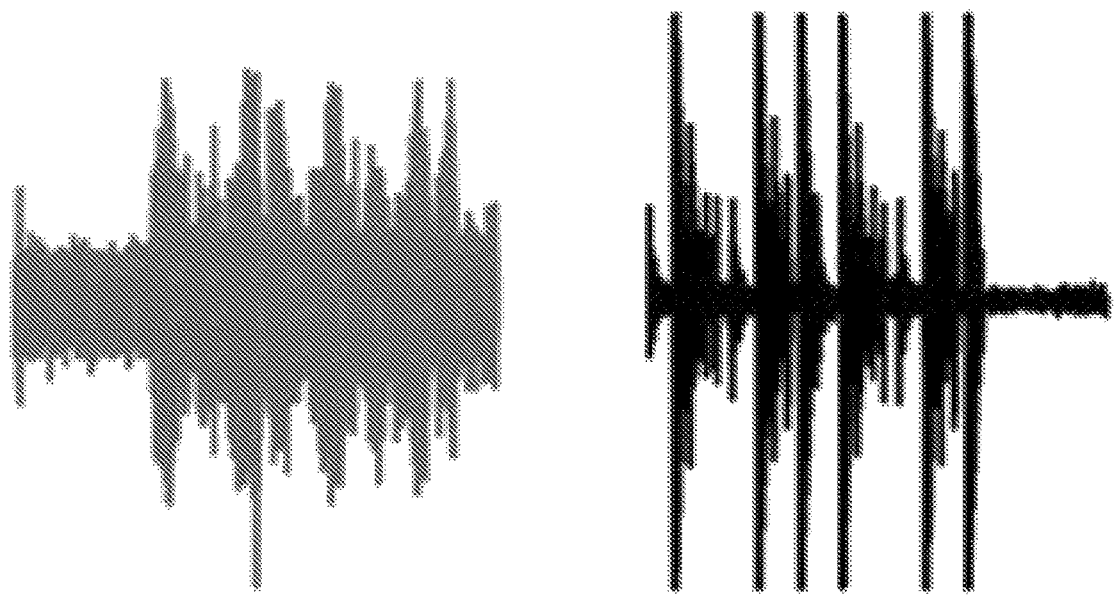
FIG. 8G is a graphical representation of the radar recovered audio waveform $\hat{x}_1(t)$ from sound source $S_1$.
FIG. 8H is a graphical representation of the original audio waveform $x_1(t)$ from sound source $S_1$.

FIG. 8E is a spectrogram of a radar result for remote recovery of the acoustic signal from the further sound source $S_1$ of FIG. 7. FIG. 8F is a spectrogram of the original audio signal from sound source $S_1$. FIG. 8G is a graphical representation of the radar recovered audio waveform $\hat{x}_1(t)$ from sound source $S_1$. FIG. 8H is a graphical representation of the original audio waveform $x_1(t)$ from sound source $S_1$.

In particular, the closer sound source $S_2$ has a triangular temporal-spectral content since the loudness increases over time. More spectral harmonic structures show up at later time. The recovered radar spectrogram (FIG. 8A) is very similar to the reference audio spectrogram (FIG. 8B). The amplitude of the radar recovered sound wave (FIG. 8C) increases over time as expected but not all details are recovered (FIG. 8D). While the temporal-spectral content in the sound source $S_1$ has a square shape, both the radar spectrogram and the waveform resemble the audio reference. Better recovery of the acoustic waveform of $S_1$ is observed because this sound is played by a much larger/louder speaker resulting in a larger surface vibration though it is located at a slightly further distance.

C. Evaluation Setup 3: See-Through Barriers

Figure 9:
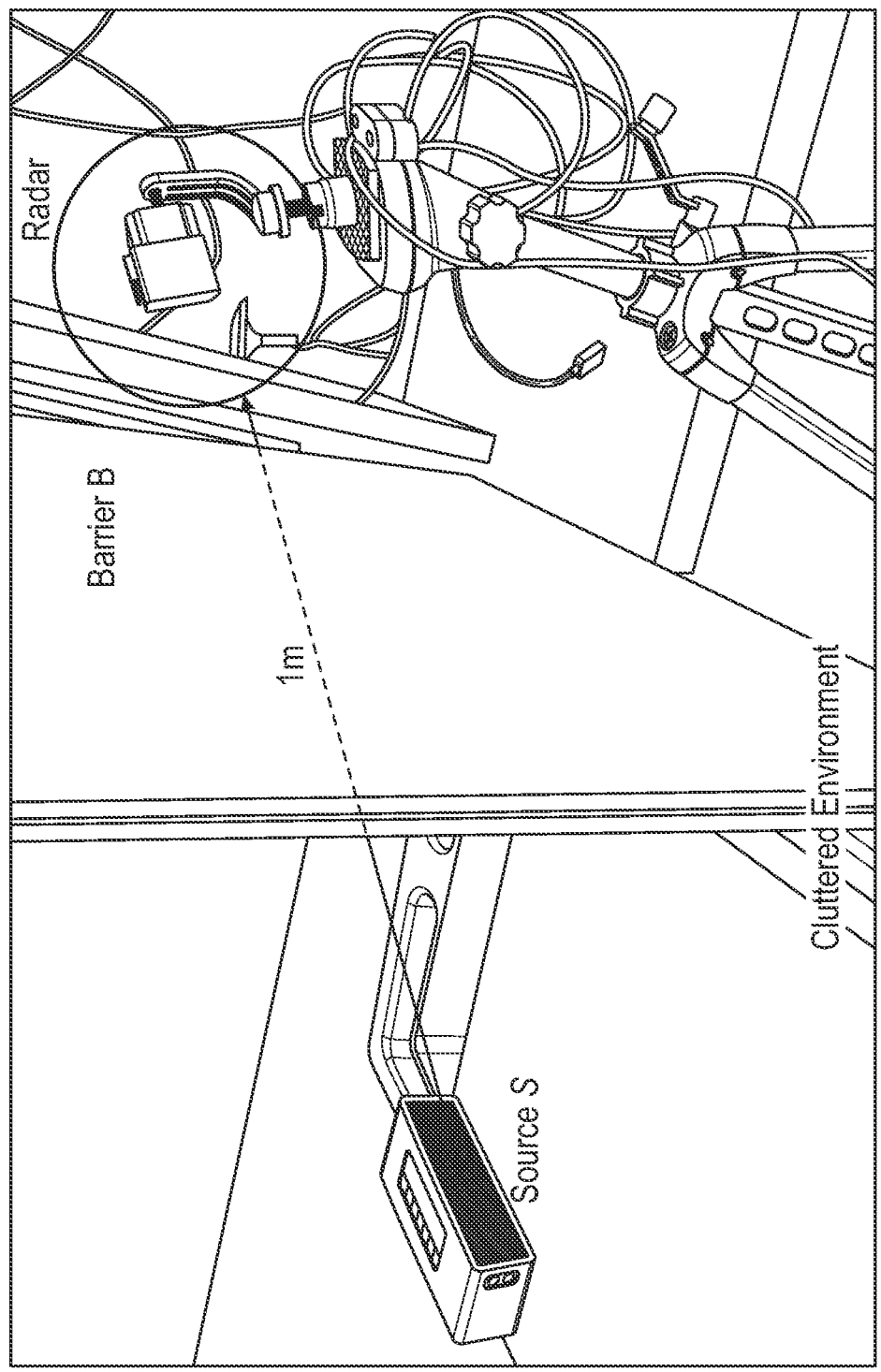
FIG. 9 is an image of the third evaluation setup, which recovers an acoustic signal through a wall or other barrier.

FIG. 9 is an image of the third evaluation setup, which recovers an acoustic signal through a wall or other barrier. Unlike light, microwave signals penetrate dielectric medium, such as clothes, glass, plastic, dry wood, wall, etc. This implies this setup can be utilized to surveil vibrating targets that are beyond line of sight (e.g., not directly observable through sound or light waves), a regime where cameras fail. Here, the ability to reconstruct an audio signal x(t) where the source S is obstructed by a non-conducting barrier B is demonstrated.

FIG. 10A is a spectrogram of a radar result for remote recovery of the acoustic signal from FIG. 9. FIG. 10B is a spectrogram of the original audio signal. FIG. 10C is a graphical representation of the radar recovered audio waveform. FIG. 10D is a graphical representation of the original audio waveform.

Despite the non-line-of-sight environment, the major spectral features and the temporal features are recovered in FIGS. 10A and 10C by comparing to the audio reference in FIGS. 10B and 10D. There are nine sound symbols corresponding to the nine distinct peaks in the audio waveform (FIG. 10D). Similarly, the radar recovered waveform (FIG. 10C) has nine spikes with a significantly reduced signal signal-to-noise ratio (SNR) due to energy loss in this blocked environment compared to the previous two evaluations. It is interesting to see that the most significant energy in the radar spectrogram is the low frequency content around 190 Hz while in the audio spectrogram it is 2nd-order harmonics around 380 Hz.

V. Method for Remote Recovery of an Acoustic Signal

Figure 11:
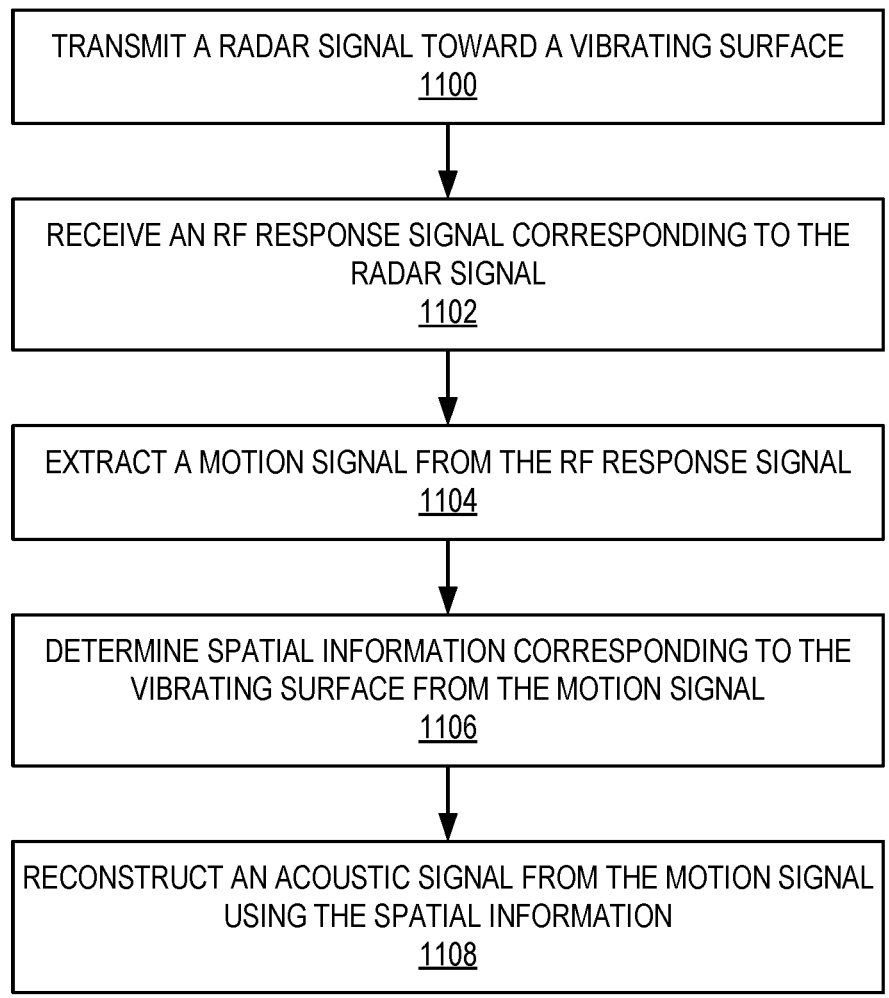
FIG. 11 is a flow diagram illustrating a process for remote recovery of an acoustic signal.

FIG. 11 is a flow diagram illustrating a process for remote recovery of an acoustic signal. The process begins at operation 1100, with transmitting a radar signal toward a vibrating surface. The process continues at operation 1102, with receiving an RF response signal corresponding to the radar signal. In an exemplary aspect, the radar sensor 14 of FIG. 2 sends a series of wideband radar impulses and receives the RF response signal. The process continues at operation 1104, with extracting a motion signal from the RF response signal. The process continues at operation 1106, with determining spatial information corresponding to the vibrating surface from the motion signal. The process continues at operation 1108, with reconstructing an acoustic signal from the motion signal using the spatial information.

Although the operations of FIG. 11 are illustrated in a series, this is for illustrative purposes and the operations are not necessarily order dependent. Some operations may be performed in a different order than that presented. Further, processes within the scope of this disclosure may include fewer or more steps than those illustrated in FIG. 11.

VI. Computer System

Figure 12:
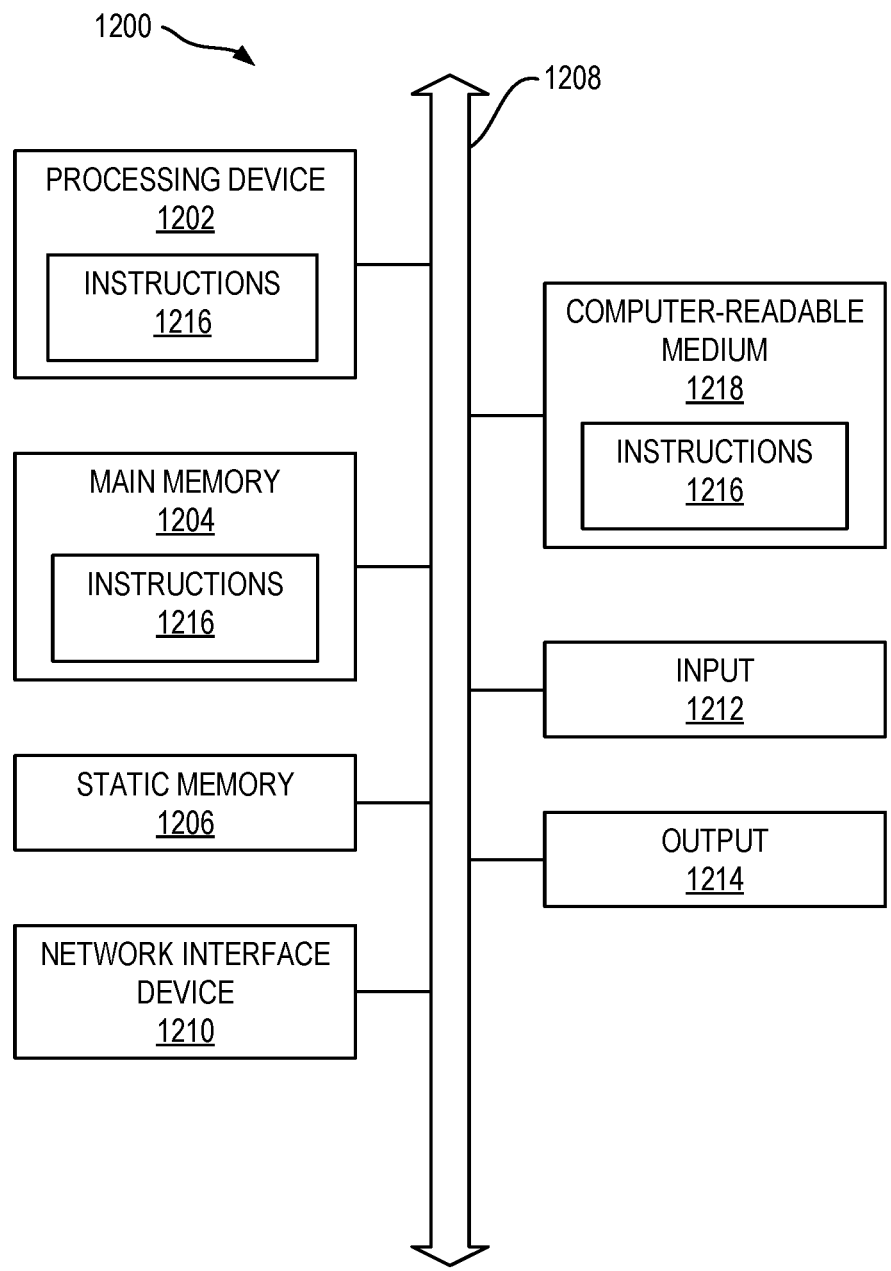
FIG. 12 is a schematic diagram of a generalized representation of an exemplary computer system that could be used to perform any of the methods or functions described above, such as remote recovery of an acoustic signal.

FIG. 12 is a schematic diagram of a generalized representation of an exemplary computer system 1200 that could be used to perform any of the methods or functions described above, such as remote recovery of an acoustic signal. In some examples, the RF device 12 of FIG. 2 is implemented as the computer system 1200 or a component of the computer system 1200. In this regard, the computer system 1200 may be a circuit or circuits included in an electronic board card, such as, a printed circuit board (PCB), a server, a personal computer, a desktop computer, a laptop computer, an array of computers, a personal digital assistant (PDA), a computing pad, a mobile device, or any other device, and may represent, for example, a server or a user's computer.

The exemplary computer system 1200 in this embodiment includes a processing device 1202 or processor, a main memory 1204 (e.g., read-only memory (ROM), flash memory, dynamic random access memory (DRAM), such as synchronous DRAM (SDRAM), etc.), and a static memory 1206 (e.g., flash memory, static random access memory (SRAM), etc.), which may communicate with each other via a data bus 1208. Alternatively, the processing device 1202 may be connected to the main memory 1204 and/or static memory 1206 directly or via some other connectivity means. In an exemplary aspect, the processing device 1202 could be used to perform any of the methods or functions described above.

The processing device 1202 represents one or more general-purpose processing devices, such as a microprocessor, central processing unit (CPU), or the like. More particularly, the processing device 1202 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 1202 is configured to execute processing logic in instructions for performing the operations and steps discussed herein.

The various illustrative logical blocks, modules, and circuits described in connection with the embodiments disclosed herein may be implemented or performed with the processing device 1202, which may be a microprocessor, field programmable gate array (FPGA), a digital signal processor (DSP), an application-specific integrated circuit (ASIC), or other programmable logic device, a discrete gate or transistor logic, discrete hardware components, or any combination thereof designed to perform the functions described herein. Furthermore, the processing device 1202 may be a microprocessor, or may be any conventional processor, controller, microcontroller, or state machine. The processing device 1202 may also be implemented as a combination of computing devices (e.g., a combination of a DSP and a microprocessor, a plurality of microprocessors, one or more microprocessors in conjunction with a DSP core, or any other such configuration).

The computer system 1200 may further include a network interface device 1210. The computer system 1200 also may or may not include an input 1212, configured to receive input and selections to be communicated to the computer system 1200 when executing instructions. The input 1212 may include, but not be limited to, a touch sensor (e.g., a touch display), an alphanumeric input device (e.g., a keyboard), and/or a cursor control device (e.g., a mouse). In an exemplary aspect, the radar sensor of FIG. 2 is an input 1212 to the computer system 1200. The computer system 1200 also may or may not include an output 1214, including but not limited to a display, a video display unit (e.g., a liquid crystal display (LCD) or a cathode ray tube (CRT)), or a printer. In some examples, some or all inputs 1212 and outputs 1214 may be combination input/output devices. In an exemplary aspect, the radar sensor of FIG. 2 is also an output 1214 of the computer system 1200.

The computer system 1200 may or may not include a data storage device that includes instructions 1216 stored in a computer-readable medium 1218. The instructions 1216 may also reside, completely or at least partially, within the main memory 1204 and/or within the processing device 1202 during execution thereof by the computer system 1200, the main memory 1204, and the processing device 1202 also constituting computer-readable medium. The instructions 1216 may further be transmitted or received via the network interface device 1210.

While the computer-readable medium 1218 is shown in an exemplary embodiment to be a single medium, the term "computer-readable medium" should be taken to include a single medium or multiple media (e.g., a centralized or distributed database, and/or associated caches and servers) that store the one or more sets of instructions 1216. The term "computer-readable medium" shall also be taken to include any medium that is capable of storing, encoding, or carrying a set of instructions for execution by the processing device 1202 and that causes the processing device 1202 to perform any one or more of the methodologies of the embodiments disclosed herein. The term "computer-readable medium" shall accordingly be taken to include, but not be limited to, solid-state memories, optical medium, and magnetic medium.

The operational steps described in any of the exemplary embodiments herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary embodiments may be combined.

Those skilled in the art will recognize improvements and modifications to the preferred embodiments of the present disclosure. All such improvements and modifications are considered within the scope of the concepts disclosed herein and the claims that follow.

What is claimed is:

1. A method for remote recovery of an acoustic signal, the method comprising:
   transmitting a radar signal toward a passively vibrating surface that is separated from an indirectly observed active acoustic source;
   receiving a radio frequency (RF) response signal corresponding to the radar signal;
   extracting a surface motion signal from the RF response signal;
   determining spatial information corresponding to the passively vibrating surface from the surface motion signal; and
   reconstructing an acoustic signal from the surface motion signal using the spatial information, wherein the acoustic signal originates from the indirectly observed active acoustic source.

2. The method of claim 1, wherein the radar signal comprises a series of wideband radar impulses.

3. The method of claim 1, wherein the spatial information comprises at least one of an angle to the passively vibrating surface, a range to the passively vibrating surface, and a Doppler frequency shift due to the passively vibrating surface.

4. The method of claim 3, wherein the Doppler frequency shift is a large-scale Doppler frequency shift.

5. The method of claim 3, wherein the Doppler frequency shift is a micro-Doppler frequency shift.

6. A radio frequency (RF) device, comprising:
   a radar sensor configured to receive a radio frequency (RF) response signal, corresponding to a radar signal transmitted to one or more passively vibrating surfaces that are separated from an indirectly observed active acoustic source; and
   a processing circuit coupled to the radar sensor and configured to recover an acoustic signal by:
      extracting a surface motion signal for the one or more passively vibrating surfaces from the RF response signal;
      determining spatial information corresponding to the one or more passively vibrating surfaces from the surface motion signal; and
      using the spatial information to recover the acoustic signal from the surface motion signal, wherein the acoustic signal originates from the indirectly observed active acoustic source.

7. The RF device of claim 6, wherein the radar sensor is further configured to transmit the radar signal, and the radar signal comprises a wideband radar signal.

8. The RF device of claim 6, wherein the spatial information comprises at least one of an angle to each of the one or more passively vibrating surfaces, a range to each of the one or more passively vibrating surfaces, and a Doppler frequency shift due to each of the one or more passively vibrating surfaces.

9. A system for remote recovery of an acoustic signal, comprising:
   a radar sensor configured to receive a radio frequency (RF) response signal, corresponding to a radar signal transmitted to a passively vibrating surface that is separated from an indirectly observed active acoustic source;
a database configured to store the RF response signal; and
a processing circuit coupled to the database and configured to:
  extract a surface motion signal for the passively vibrating surface from the RF response signal;
  determine spatial information corresponding to the passively vibrating surface from the motion signal, the spatial information comprising at least one of a range to the vibrating surface, an angle to the vibrating surface, and a Doppler frequency shift associated with the vibrating surface; and
  reconstruct the acoustic signal from the motion signal using the spatial information, wherein the acoustic signal originates from the indirectly observed active acoustic source.

* * * * *